United States Patent [19]

Perlman

[11] Patent Number: 4,883,597
[45] Date of Patent: Nov. 28, 1989

[54] HYDROPHOBIC MEMBRANE FOR DRYING GEL MATRICES

[75] Inventor: Daniel Perlman, Arlington, Mass.

[73] Assignee: Brandeis University, Waltham, Mass.

[21] Appl. No.: 264,097

[22] Filed: Oct. 28, 1988

[51] Int. Cl.$^4$ .............................................. B01D 13/00
[52] U.S. Cl. ................................. 210/640; 204/182.8; 210/490
[58] Field of Search ...................... 204/182.8; 210/490, 210/500.3, 500.29, 640

[56] References Cited

U.S. PATENT DOCUMENTS

| | | | |
|---|---|---|---|
| 4,210,529 | 7/1980 | Petersen | 210/500.29 X |
| 4,214,994 | 7/1980 | Kitano et al. | 210/490 |
| 4,419,242 | 12/1983 | Cheng et al. | 210/500.3 X |
| 4,668,363 | 5/1987 | Gebott et al. | 204/182.8 |
| 4,687,968 | 8/1987 | Frayer | 313/509 |

OTHER PUBLICATIONS

Cockerill, "Two Methods That Facilitate Autoradiography of Small $^{32}$P-Labeled DNA Fragments following Electrophoresis in Agarose Gels", Analytical Biochemistry, 168:451-454 (1988).
FMC, Gelbond Film for Agarose Gels, advertisement.

Primary Examiner—Frank Spear

[57] ABSTRACT

A method for removing liquid from a gel matrix including the steps of providing a hydrophobic water vapor-permeable membrane adapted to transmit water vapor and to resist passage of liquid water by capillary diffusion. The membrane and gel matrix are contacted together and subjected to a vacuum to remove water vapor from the gel matrix through the membrane. Liquid is removed from the gel matrix, and the gel matrix simultaneously adheres to the membrane.

16 Claims, No Drawings

HYDROPHOBIC MEMBRANE FOR DRYING GEL MATRICES

BACKGROUND OF THE INVENTION

This invention concerns the use of hydrophobic membranes for drying gel matrices, for example, polyacrylamide or agarose gels commonly used in laboratories for separating DNA and proteins.

Gel electrophoresis in polyacrylamide gels and agarose gels is a common procedure for separation of DNA, RNA and polypeptides. After these materials have been separated within the gel matrix it is common to dry the matrix inorder to either preserve the matrix itself or to detect bands of protein or nucleic acid within the gels. For example, in DNA sequencing procedures, a thin (0.4 millimeter) polyacrylamide gel is placed onto Whatman 3 MM TM filter paper and dried until it is less than about 0.05 mm in thickness. The drying procedure entails positioning the gel matrix on the filter paper and placing the filter paper-gel matrix combination within a vacuum-assisted drying apparatus where it is subjected to a vacuum and generally heated to remove liquid from the matrix.

In place of filter paper, gels are also dried on a hydrophilic cellulose dialysis membrane, on a hydrophilic nylon membrane such as a Zeta-probe TM Membrane (Cockerill, Analytical Biochemistry, 168:451, 1988), and on chemically interactive membranes which are bonded to the gel during casting, that is, prior to electrophoresis of the components to be separated in the gel. These latter membranes include Gel Bond ® and Gel Bond ® PAG films (manufactured by FMC Corp.) which are polyester films carrying chemical coatings for binding agarose and polyacrylamide gels, respectively.

SUMMARY OF THE INVENTION

In a first aspect, the invention features a method for removing liquid from a gel matrix including the steps of providing a hydrophobic water vapor permeable membrane adapted to transmit water vapor and to resist passage of liquid water by capillary diffusion. The membrane and matrix are contacted together and subjected to a vacuum to remove water vapor from the matrix through the membrane. Liquid is removed from the matrix, and the matrix simultaneously adheres to the membrane.

In a second aspect, the invention features a gel matrix adherently fixed to a hydrophobic water vapor-permeable membrane adapted to transmit water vapor and to resist passage of liquid water by capillary diffusion.

In preferred embodiments of the above aspects, the gel is dried within a vacuum assisted gel drying apparatus; the membrane is formed from a permeable polyolefin membrane comprising a polypropylene material, a polyethylene material, a high density non-woven polyethylene fiber material, a hydrophilic material treated to become hydrophobic, for example, silicone-impregnated filter paper; and the permeable polyolefin membrane is preferably treated by spark-discharge and/or with an antistatic agent. Most preferably the membrane is formed from Tyvek TM.

In general, the invention features the use of a polyolefin, or other substantially hydrophobic material in the matrix of a water vapor permeable membrane which is resistant to passage of liquid water by capillary action, for the purpose of drying and analyzing aqueous electrophoretic slab gels. The membrane functions as an adherent but non absorbent substrate support for the slab gel during vacuum drying of the gel. The membrane may also be used in apparatus which combines vacuum and heat drying of the gel. Because the membrane is non absorbent and substantially resistant to capillary diffusion of water-soluble materials from the slab gel, migration of substances held within the gel matrix is prevented. Thus, sharper nucleic acid or protein bands are produced in the dried gel.

Despite the hydrophobic character of the membranes of this invention, aqueous slab gels are surprisingly found to adherently bind to the membrane after drying. The membranes also tend to block the wet gel from significantly entering and mixing with the membrane matrix. As a result, macromolecular diffusion is reduced during drying. Such diffusion occurs during drying on hydrophilic filter paper and may result in loss of macromolecules fractionated in the gel during electrophoresis. Cockerill, supra. It may also decrease resolution of the fractionated macromolecules due to capillary diffusion spreading the molecules within the paper. Unlike hydrophilic membranes such as Whatman 3 MM TM filter paper, the membranes of the present invention are relatively cheap and have little or no affinity for rehydrating moisture present in the ambient air following the drying process. Such rehydrating moisture can, in the case of gels dried on 3 MM paper, result in the gel becoming sticky and then adhering to photographic film, for example, used for gel autoradiography.

The present invention exploits a new method of gel drying by which water vapor is directly liberated from the gel and is pulled by a vacuum through the inert non-absorbent hydrophobic polyethylene support. This process helps avoid capillary diffusional loss of gel-fractionated molecules via the liquid phase occurring during blot drying on filter paper or on other hydrophilic surfaces. Since the gel is dried on the surface of the membrane rather than being partially absorbed into the membrane, subsequent analysis of the gel is improved. In particular, molecular resolution using autoradiography and fluorescence detection methods, which rely upon detection devices (such as photographic film) placed in intimate contact with the gel, are improved using gels mounted on hydrophobic membranes rather than on hydrophilic paper. These analytical methods rely upon either radiation or light emerging from molecular species such as radioactively labeled and fluorescently labeled protein and DNA molecules within the gel.

An additional advantage of the hydrophobic support matrix over hydrophilic paper, is its increased chemical resistance and dimensional stability in the presence of water and other liquids and vapors. Hydrophilic filter paper, such as Whatman 3 MM TM, generally expands on contact with water and contributes to undesirable dimensional distortion of the dried gel. Further, strong caustic materials, such as sodium hydroxide, encountered in denaturing gels may weaken the filter paper. The hydrophobic membranes including the polyolefin materials of the present invention are not affected by contact with water or caustic materials.

Other features and advantages of the invention will be apparent from the following description of the preferred embodiments thereof, and from the claims.

DESCRIPTION OF THE PREFERRED EMBODIMENT

Hydrophobic Membrane

Any hydrophobic membrane which is water vapor-permeable, such that a gel matrix may be dried within a reasonable time on a gel drying apparatus, is suitable. The hydrophobic membrane is also resistant to passage of water by capillary diffusion such that diffusion of protein or nucleic acid bands from the gel matrix is substantially prevented. Thus, the hydrophobic membrane causes separated biological molecules to preferentially remain within the gel matrix, rather than entering the hydrophobic membrane. Examples of such membranes are described in Frayer, U.S. Pat. No. 4,687,968.

Preferred hydrophobic membranes alleviate capillary diffusion, provide a strong, durable gel support which is chemically inert and tolerate temperatures up to about 100° C., as for example encountered in some gel heat-drying devices. While substantially excluding the gel from within the membrane matrix, the membrane should retain the gel as a smooth dried layer on that membrane surface.

One example of such a membrane is the non-woven high density polyethylene fiber material known as Tyvek TM (manufactured by DuPont). Polypropylene semi-permeable membranes and other such membranes formed from intrinsically hydrophobic materials are also suitable for use in the invention. Hydrophilic membranes such as Whatman 3 MM TM filter paper whose matrix has been treated (e.g., impregnated with dimethyl dichlorosilane) to become substantially hydrophobic, are also suitable for use in the present invention.

The membrane may be pretreated to enhance its useful properties. For example, Tyvek TM was obtained from DuPont. The material had been subjected to spark-discharge, and treated with an antistatic agent, as described by DuPont in "Tyvek TM a guide to properties and end uses" (E.I. DuPont Co., Fibers Department Industrial Products Division, Wilmington, Del.; 1985). Type 10 Tyvek TM styles 1079 and 1085D, which are relatively stiff and heavy varieties of spark-discharge and antistatic treated Tyvek TM materials are preferred.

Methods

In one example of the use of Tyvek TM as a gel drying membrane, an aqueous polyacrylamide electrophoretic gel (10% by weight polyacrylamide) used in electrophoresis of DNA fragments of varying sizes, was transferred while still moist from a glass plate to a Tyvek TM membrane, style 1085D, by direct contact between the gel and the membrane. Surface tension between the moist gel and the non absorbent membrane facilitated this transfer. The gel membrane bilayer was then subjected to vacuum and heat drying for 30 minutes on a standard commercial gel dryer (Hoeffer Co. model SE1140 slab gel drier) set at a temperature of 80° C. The geometry of drying the gel on top of the Tyvek TM membrane was identical to that normally used with standard Whatman 3 MM TM filter paper. Only water vapor from the gel was pulled downward through the Tyvek TM membrane. During the process of heating and drying the gel under vacuum the gel became bonded to the membrane. The gel which had been dried on the Tyvek TM membrane remained prominently on the surface of the membrane rather than becoming absorbed into and mixed with the membrane matrix material. Using a colored tracking dye in the gel, no wicking of liquid water through the membrane could be observed. In contrast, an identical gel dried on Whatman 3 MM TM filter paper showed tracking dye evidence of capillary diffusion of liquid through the filter and loss of separated molecular materials held within the gel.

Other embodiments are within the following claims.

I claim:

1. A method for removing liquid from an electrophoresis gel matrix comprising the steps of:
providing a water vapor-permeable membrane adapted to transmit water vapor and to resist passage of liquid water by capillary diffusion, said membranes being hydrophobic,
contacting said gel matrix with said membrane, and
subjecting said gel matrix and membrane to a vacuum to remove water vapor from said matrix through said membrane, whereby liquid is removed from said matrix and said matrix adheres to said membrane.

2. The method of claim 1 wherein said subjecting step comprises placing said gel matrix and said membrane within a vacuum assisted gel drying apparatus.

3. The method of claim 1 wherein said providing step comprises providing a membrane formed from a polyolefin material.

4. The method of claim 1 wherein prior to said providing step said membrane is formed from high density non-woven polyethylene fibers and is treated by spark-discharge.

5. The method of claim 1 wherein prior to said providing step said membrane is formed from a hydrophilic material and treated to become hydrophobic.

6. The method of claim 5 wherein said membrane is formed from filter paper.

7. The method of claim 4 wherein said membrane is treated with an antistatic agent.

8. The method of claim 1, wherein said membrane if formed from a non-woven high density polyethylene fiber material.

9. A gel matrix comprising material electrophoresed within said matrix adherently fixed to a water vapor-permeable membrane adapted to transmit water vapor and to resist passage of liquid water by capillary diffusion, said membrane being hydrophobic.

10. The gel matrix of claim 9 wherein said membrane is formed from a polyolefin.

11. The gel matrix of claim 10 wherein said polyolefin is chosen from polypropylene and polyethylene.

12. The gel matrix of claim 9 wherein said membrane is formed from high density non-woven polyethylene fibers treated by spark-discharge.

13. The gel matrix of claim 9 wherein said membrane is formed from a hydrophilic membrane treated to become hydrophobic.

14. The gel matrix of claim 13 wherein said membrane is formed from filter paper.

15. The gel matrix of claim 9 wherein said membrane is treated with an antistatic agent.

16. A gel matrix of claim 9 wherein said membrane is formed from a non-woven high density polyethylene fiber material.

* * * * *